United States Patent [19]

Nicholson et al.

[11] Patent Number: 5,552,536
[45] Date of Patent: Sep. 3, 1996

[54] DNA ENCODING PRECURSOR OF INTERLEUKIN-1 BETA CONVERTING ENZYME - RELATED CYSTEINE PROTEINASE III (ICE REL-III)

[75] Inventors: Donald W. Nicholson, Montreal; Ambereen Ali, Pierrefonds; Neil A. Munday, Guelph; John P. Vaillancourt, Pierrefonds, all of Canada

[73] Assignee: Merck Frosst Canada, Inc., Quebec, Canada

[21] Appl. No.: 224,930

[22] Filed: Apr. 8, 1994

[51] Int. Cl.$^6$ .................... C07H 21/02; C07H 21/04; C12N 15/70; C12N 5/10
[52] U.S. Cl. .................... 536/23.1; 435/240.2; 435/320.1
[58] Field of Search .................. 536/22.1, 23.1, 536/24.3; 435/6, 320.1, 240.2, 252.3

[56] References Cited

U.S. PATENT DOCUMENTS 5,416,013  5/1995  Black et al. ............................ 435/226

FOREIGN PATENT DOCUMENTS

WO93/25685  12/1993  WIPO.
WO93/25694  12/1993  WIPO.
WO94/06906  3/1994  WIPO.

OTHER PUBLICATIONS

Barinaga, M. "Cell Suicide: by ICE, Not Fire", Science, vol. 263, Feb. 11, 1994 pp. 754–756.
Cerretti, D. P. et al. "Molecular Cloning of the Interleukin–1 beta converting Enzyme", Science, vol. 256, 3 Apr. 1992 pp. 97–100.
Gagliardini, V. et al., "Prevention of Vertebrate Neuronal Death by the crmA Gene", Science, vol. 263, 11 Feb. 1994, pp. 826–828.
Miura, M. et al., "Induction of Apoptosis in Fibroblasts by IL–1 Beta–Converting Enzyme, a Mammalian Homolog of the C. elegans Cell Death Gene ced–3", Cell, vol. 75, Nov. 19, 1993, pp. 653–660.

Thornberry, N. A. et al. "A Novel Heterodimeric Cysteine Protease is Required for Interleukin–1 Beta Processing in Monocyles", Nature, vol. 356, Apr. 30, 1992, pp. 768–774.
Yuan, J. et al., "The C. elegans Cell Death Gene ced–3 Encodes of Protein Similar to Mammalian Interleukin 1 Beta–Converting Enzyme", Cell, vol. 75, Nov. 19, 1993, pp. 641–652.
New England Biolabs Catalog (1993–1994), p. 92.
Munday et al, (1995), "Molecular cloning and pro–apoptotic activity if $ICE_{rel}II$ and $ICE_{rel}III$, members of the ICE/CED–3 family of cysteine proteases", J. Biol. Chem. 270(26): 15870–15876.
Kamens et al, (1995), "Identification and characterization of ICH–2, a novel member of the interleukin–1B–converting enzyme family of cysteine proteases", J. Biol. Chem. 270(25): 15250–15256.
Alnemri et al, (1995), "Cloning and expression of four novel isoforms of human interleukin–1B converting enzyme with different apoptoic activities", J. Biol. Chem. 270(9):4312–4317.
Fancheu et al, (1995), "A novel human protease similar to the interleukin–1B converting enzyme induces apoptosis in transfected cells", EMBO J. 14(9): 1914–1922.

*Primary Examiner*—Stephanie W. Zitomer
*Assistant Examiner*—Jeffrey Fredman
*Attorney, Agent, or Firm*—Christine E. Carty; Jack L. Tribble

[57] ABSTRACT

A complementary DNA (cDNA) encoding full length form of $ICE_{rel}$-III is identified, sequenced and isolated. The cDNA is cloned into expression vectors for expression in recombinant hosts. The cDNA is useful to produce recombinant full length $ICE_{rel}$-III. The cDNA and the recombinant $ICE_{rel}$-III protein derived therefrom are useful in diagnostic kits, laboratory reagents and assays. The cDNA and the recombinant $ICE_{rel}$-III protein may be used to identify compounds that affect $ICE_{rel}$-III function, inflammation and cell apoptosis. $ICE_{rel}$-III function, inflammation and cell apoptosis may also be modulated by $ICE_{rel}$-III antisense or gene therapy.

4 Claims, 6 Drawing Sheets

```
     CGGCAAAAAAAAAAAGGCCGTAAGAATTTTGAAGCTATGTTCAAAGGTATCCTTCAGAGTGG
  1  +--------+--------+--------+--------+--------+--------+  60
     GCCGTTTTTTTTTTCCGCATTCTTAAAACTTCGATACAAGTTTCCATAGGAAGTCTCACC
                                  MetPheLysGlyIleLeuGlnSerGl
```

```
     ATTGGATAACTTCGTGATAAACCACATGCTAAAGAACAACGTGGCTGGACAAACATCTAT
 61  +--------+--------+--------+--------+--------+--------+  120
     TAACCTATTGAAGCACTATTTGGTGTACGATTTCTTGTTGCACCGACCTGTTTGTAGATA
     yLeuAspAsnPheValIleAsnHisMetLeuLysAsnAsnValAlaGlyGlnThrSerIl
```

```
     CCAGACCCTAGTACCTAATACGGATCAAAAGTCGACCAGTGTAAAAAAAGACAACCACAA
121  +--------+--------+--------+--------+--------+--------+  180
     GGTCTGGGATCATGGATTATGCCTAGTTTTCAGCTGGTCACATTTTTTTCTGTTGGTGTT
     eGlnThrLeuValProAsnThrAspGlnLysSerThrSerValLysLysAspAsnHisLy
```

```
     AAAAAAAAACAGTTAAGATGTTGGAATACCTGGGCAAAGATGTTCTTCATGGTGTTTTTAA
181  +--------+--------+--------+--------+--------+--------+  240
     TTTTTTTTGTCAATTCTACAACCTTATGGACCCGTTTCTACAAGAAGTACCACAAAAATT
     sLysLysThrValLysMetLeuGluTyrLeuGlyLysAspValLeuHisGlyValPheAs
```

```
     TTATTTGGCAAAACACGATGTTCTGACATTGAAGGAAGAGGAAAAGAAAAAATATTATGA
241  +--------+--------+--------+--------+--------+--------+  300
     AATAAACCGTTTTGTGCTACAAGACTGTAACTTCCTTCTCCTTTTCTTTTTTATAATACT
     nTyrLeuAlaLysHisAspValLeuThrLeuLysGluGluGluLysLysTyrTyrAs
```

```
     TGCCAAAATTGAAGACAAGGCCCTGATCTTGGTAGACTCTTTGCCGAAAGAATCGCGTGCC
301  +--------+--------+--------+--------+--------+--------+  360
     ACGGTTTTAACTTCTGTTCCGGGACTAGAACCATCTGAGAAACGCTTTCTTAGCGCACCG
     pAlaLysIleGluAspLysAlaLeuIleLeuValAspSerLeuArgLysAsnArgValAl
```

```
     TCATCAAATGTTTACCCAAACACTTCTCAATATGGACCAAAAGATCACCAGTGTAAAACC
361  +--------+--------+--------+--------+--------+--------+  420
     AGTAGTTTACAAATGGGTTTGTGAAGAGTTATACCTGGTTTTCTAGTGGTCACATTTTGG
     aHisGlnMetPheThrGlnThrLeuLeuAsnMetAspGlnLysIleThrSerValLysPr
```

```
     TCTTCTGCAAATCGAGGCTGGACCACCTGAGTCAGCAGAATCTACAAATATACTCAAACT
421  +--------+--------+--------+--------+--------+--------+  480
     AGAAGACGTTTAGCTCCGACCTGGTGGACTCAGTCGTCTTAGATGTTTATATGAGTTTGA
     oLeuLeuGlnIleGluAlaGlyProProGluSerAlaGluSerThrAsnIleLeuLysLe
```

FIG.1A

```
              TTGTCCTCGTGAAGAATTCCTGAGACTCTGTAAAAAAAATCATGATGAGATCTATCCAAT
        481   ------+---------+---------+---------+---------+---------+     540
              AACAGGAGCACTTCTTAAGGACTCTGACACATTTTTTTTAGTACTACTCTAGATAGGTTA
              uCysProArgGluGluPheLeuArgLeuCysLysLysAsnHisAspGluIleTyrProIl

AAAAAAGAGAGAGGACCGCAGACGCCTGGCTCTCATCATATGCAATACAAAGTTTGATCA
        541   ------+---------+---------+---------+---------+---------+     600
              TTTTTTCTCTCTCCTGGCGTCTGCGGACCGAGAGTAGTATACGTTATGTTTCAAACTAGT
              eLysLysArgGluAspArgArgArgLeuAlaLeuIleIleCysAsnThrLysPheAspHi

CCTGCCTGCAAGGAATGGGGCTCACTATGACATCGTGGGGATGAAAAGGCTGCTTCAAGG
        601   ------+---------+---------+---------+---------+---------+     660
              GGACGGACGTTCCTTACCCCGAGTGATACTGTAGCACCCCTACTTTTCCGACGAAGTTCC
              sLeuProAlaArgAsnGlyAlaHisTyrAspIleValGlyMetLysArgLeuLeuGlnGl

CCTGGGCTACACTGTGGTTGACGAAAAGAATCTCACAGCCAGGGATATGGAGTCAGTGCT
        661   ------+---------+---------+---------+---------+---------+     720
              GGACCCGATGTGACACCAACTGCTTTTCTTAGAGTGTCGGTCCCTATACCTCAGTCACGA
              yLeuGlyTyrThrValValAspGluLysAsnLeuThrAlaArgAspMetGluSerValLe

GAGGGCATTTGCTGCCAGACCAGAGCACAAGTCCTCTGACAGCACGTTCTTGGTACTCAT
        721   ------+---------+---------+---------+---------+---------+     780
              CTCCCGTAAACGACGGTCTGGTCTCGTGTTCAGGAGACTGTCGTGCAAGAACCATGAGTA
              uArgAlaPheAlaAlaArgProGluHisLysSerSerAspSerThrPheLeuValLeuMe

GTCTCATGGCATCCTAGAGGGAATCTGCGGAACTGCGCATAAAAAGAAAAAACCGGATGT
        781   ------+---------+---------+---------+---------+---------+     840
              CAGAGTACCGTAGGATCTCCCTTAGACGCCTTGACGCGTATTTTTCTTTTTTGGCCTACA
              tSerHisGlyIleLeuGluGlyIleCysGlyThrAlaHisLysLysLysProAspVa

GCTGCTTTATGACACCATCTTCCAGATATTCAACAACCGCAACTGCCTCAGTCTAAAGGA
        841   ------+---------+---------+---------+---------+---------+     900
              CGACGAAATACTGTGGTAGAAGGTCTATAAGTTGTTGGCGTTGACGGAGTCAGATTTCCT
              lLeuLeuTyrAspThrIlePheGlnIlePheAsnAsnArgAsnCysLeuSerLeuLysAs

CAAACCCAAGGTCATCATTGTCCAGGCCTGCAGAGGTGAAAAACATGGGGAACTCTGGGT
        901   ------+---------+---------+---------+---------+---------+     960
              GTTTGGGTTCCAGTAGTAACAGGTCCGGACGTCTCCACTTTTTGTACCCCTTGAGACCCA
              pLysProLysValIleIleValGlnAlaCysArgGlyGluLysHisGlyGluLeuTrpVa
```

FIG. 1B

```
          CAGAGACTCTCCAGCATCCTTGGCAGTCATCTCTTCACAGTCATCTGAGAACCTGGAGGC
    961   ------+---------+---------+---------+---------+---------+  1020
          GTCTCTGAGAGGTCGTAGGAACCGTCAGTAGAGAAGTGTCAGTAGACTCTTGGACCTCCG
          lArgAspSerProAlaSerLeuAlaValIleSerSerGlnSerSerGluAsnLeuGluAl

AGATTCTGTTTGCAAGATCCACGAGGAGAAGGACTTCATTGCTTTCTGTTCTTCAACACC
   1021   ------+---------+---------+---------+---------+---------+  1080
          TCTAAGACAAACGTTCTAGGTGCTCCTCTTCCTGAAGTAACGAAAGACAAGAAGTTGTGG
          aAspSerValCysLysIleHisGluGluLysAspPheIleAlaPheCysSerSerThrPr

ACATAACGTGTCCTGGAGAGACCGCACAAGGGGCTCCATCTTCATTACGGAACTCATCAC
   1081   ------+---------+---------+---------+---------+---------+  1140
          TGTATTGCACAGGACCTCTCTGGCGTGTTCCCCGAGGTAGAAGTAATGCCTTGAGTAGTG
          oHisAsnValSerTrpArgAspArgThrArgGlySerIlePheIleThrGluLeuIleTh

ATGCTTCCAGAAATATTCTTGCTGCTGCCACCTAATGGAAATATTTCGGAACGTACAGAA
   1141   ------+---------+---------+---------+---------+---------+  1200
          TACGAAGGTCTTTATAAGAACGACGACGGTGGATTACCTTTATAAAGCCTTCCATGTCTT
          rCysPheGlnLysTyrSerCysCysCysHisLeuMetGluIlePheArgLysValGlnLy

ATCATTTGAAGTTCCACAGGCTAAAGCCCAGATGCCCACCATAGAACGAGCAACCTTGAC
   1201   ------+---------+---------+---------+---------+---------+  1260
          TAGTAAACTTCAAGGTGTCCGATTTCGGGTCTACGGGTGGTATCTTGCTCGTTGGAACTG
          sSerPheGluValProGlnAlaLysAlaGlnMetProThrIleArgAlaThrLeuTh

AAGAGATTTCTACCTCTTTCCTGGCAATTGAAAATGAAACCACAGGCAGCCCAGCCCTCC
   1261   ------+---------+---------+---------+---------+---------+  1320
          TTCTCTAAAGATGGAGAAAGGACCGTTAACTTTTACTTTGGTGTCCGTCGGGTCGGGAGG
          rArgAspPheTyrLeuPheProGlyAsnEnd

TCTGTCAACATCAAAGAGCACATTTACCAGTATAGCTTGCATAGTCAATATTTGGTATTT
   1321   ------+---------+---------+---------+---------+---------+  1380
          AGACAGTTGTAGTTTCTCGTGTAAATGGTCATATCGAACGTATCAGTTATAAACCATAAA

CAATAAAAGTAAAGACTGTAAAAAAAAAAAAAAAA
   1381   ------+---------+---------+---  1414
          GTTATTTTCATTTCTGACATTTTTTTTTTTTTTTT
```

FIG. 1C

```
  1  MFKGILQSGLDNFVINHMLKNNVAGQTSIQTLVPNTDQKSTSVKKDNHKK   50
                                        ....|  |:.:|
  1  ................................MADKVLKEKRK.        11

51  KTVKMLEYLGKDVLHGVFNYLAKHDVLTLKEEEKKKYYDAKIEDKALILV  100
     ::  :|.:.::|:::  | .  ||..|||  |  :|.: ||. |:
 12  ...LFIRSMGEGTINGLLDELLQTRVLNKEEMEKVKRENATVMDKTRALI   58

101  DS.LRKNRVAHQM............FTQTL............LNMDQKITSV  127
     ||:.|. ||:          :..||           |||::. . :
 59  DSVIPKGAQACQICITYICEEDSYLAGTLGLSADQTSGNYLNMQDSQGVL  108

128  KPL......LQIEAGPPESAESTNILKLCPREEFLRLCKKNHDEIYPIKKR  172
     ..:      :|  :::  |.|.:|.. :|||. ||  |: |.. .|||||..:
109  SSFPAPQAVQDNPAMPTSSGSEGNVKLCSLEEAQRIWKQKSAEIYPIMQK  158

173  EDRRRLALIICNTKFDHLPARNGAHYDIVGMKRLLQGLGYTVVDEKNLTA  222
     ..|  ||||||||..||  :|  |.||.  ||.||..|||.|||.|  .||||
159  SSRTRLALIICNEEFDSIPRRTGAEVDITGMTMLLQNLGYSVDVKKNLTA  208

223  RDMESVLRAFAARPEHKSSDSTFLVLMSHGILEGICGTAHKKKKPDVLLY  272
     .||.. |  ||||  |||||.||||||:|||||  |||||. | ...  ||:|  .
209  SDMTTELEAFAHRPEHKTSDSTFLVFMSHGIREGICGKKHSEQVPDILQL  258

273  DTIFQIFNNRNCLSLKDKPKVIIVQACRGEKHGELWVRDSPASLAVISSQ  322
     :.||.::|.:||  ||||||||||||:||||:...|  :|.:||.:   : :|.
259  NAIFNMLNTKNCPSLKDKPKVIIIQACRGDSPGVVWFKDSVGVSGNLSLP  308

323  SSENLEADSVCKIHEEKDFIAFCSSTPHNVSWRDRTRGSIFITELITCFQ  372
     ..|::|.|.:  | |  |||||||||||||.||||..|.||:||. ||. :|
309  TTEEFEDDAIKKAHIEKDFIAFCSSTPDNVSWRHPTMGSVFIGRLIEHMQ  358

373  KYSCCCHLMEIFRKVQKSFEVPXAKAQMPTIERATLTRDFYLFPGN*    419
     .|.|:|.:  ||||||.  |||  |  |::|||||.||.||||  ||||||:|
359  EYACSCDVEEIFRKVRFSFEQPDGRAQMPTTERVTLTRCFYLFPCH*    405
```

FIG.2

```
  1 MFKGILQSGLDNFVINHMLKNNVAGQTSIQTLVP.......NTDQKSTSV  43
    |::. .| |:. :: |:...:: .:. :::.|::       |.|  ...:.
  1 MMRQDRRSLLERNIM...MFSSHLKVDEILEVLIAKQVLNSDNGDMINSCG  48

44 KKDNHKKKTVKMLEYLGKDVLHGVFNYL...AKHDVLTLKEEEKKKYYDA  90
    . :.::..|| :: |. .:.:.:.:: |  :....:: .: |. :.  ..
 49 TVREKRREIVKAVQRRGDVAFDAFYDALRSTGHEGLAEVLEPLARSVDSN  98

91 KIEDKALILVDSLRKNR.VAHQMFTQTLLNMDQKITSVKPLLQIE.....  134
    :| .. : ..| |:.| :... :|.    :.:.||..:   .:
 99 AVEFECPMSPASHRRSRALSPAGYTSPTRVHRDSVSSVSSFTSYQDIYSR  148

135 ....................AGPPESAEST...............  144
                       :::.|.||:|.
149 ARSRSRSRALHSSDRHNYSSPPVNAFPSQPSSANSSFTGCSSLGYSSSRN  198

145 .NILKLCPREEFL...........RLCKKNHDEIYPIKKREDRRRLALII  182
    .: |  :...:::         ...: ||  .:. ...| :.|||
199 RSFSKASGPTQYIFHEEDMNFVDAPTISRVFDEKTMYRNFSSPRGMCLII  248

183 CNTKFDHLPARNGAHYDIVGMKRLLQGLGYTVVDEKNLTARDMESVLRAF  232
    |..|:::|.|||.. |  .:.:|:..:||||: ..|||:|:|  .:|.|
249 NNEHFEQMPTRNGTKADKDNLTNLFRCMGYTVICKDNLTGRGMLLTIRDF  298

233 AARPEHKSSDSTFLVLMSHGILEGICGTAHKKKKPDVLLYDTIFQIFNNR  282
    | :..| :||.:||::|||  :.|.|... ..     ..|::::|.
299 AKHESH..GDSAILVILSHGEENVIIGVDDIPIST.....HEIYDLLNAA  341

283 NCLSLKDKPKVIIVQACRGEKHGELW.VRDSPASLAVISSQSSENLEADS  331
    |.. | :|||:::|||||||||:::: : |  ||..:::.: .:..:| ::.
342 NAPRLANKPKIVFVQACRGERRDNGFPVLDSVDGVPAFLRRGWDNRDGPL  391

332 V..............CKIHEEKDFIAFCSSTPHNVSWRDRTRGSIFITEL  367
                  |  ..: |:: :..|:: ||||:...||| ||  .:
392 FNFLGCVRPQVQQVWRKKPSQADILIRYATTAQYVSWRNSARGSWFIQAV  441

368 ITCFQKYSCCCHLMEIFRKVQKSFEVPXAKAQMPTIER......ATLTRD  411
    ...| ...  .::|:: .|.|..... ...| ..|  :    . | :.
442 CEVFSTHAKDMDVVELLTEVNKKVACGFQTSQGSNILKQMPEMTSRLLKK  491

412 FYLFPGN*.....  419
    ||::|:.
492 FYFWPEARNSAV*  504
```

FIG.3

```
201 VGMKRLLQGLGYTVVDEKNLTARDMESVLRAFAARPEHKSSDSTFLVLMS 250
             :|  . . |..:|:|.|. :|
  1 ........................MLTVQVYRTSQKCSSSKHVV...  20

251 HGILEGICGTAHKKKKPDVLLYDTIFQIFNNRNCLSLKDKPKVIIVQACR 300
    ..:|:..:... .  .|.:|||:|  .:
 21 EVLLDPLGTSFCSLLPPPLLLYETDRGV.....................  48

301 GEKHGELWVRDSPASLAVISSQSSENLEADSVCKIHEEKDFIAFCSSTPH 350
    :..:::    :||:       :..:|... |.   :::.  .|:|. ..:  .
 49 .DQQDGKNHTQSPG.....CEESDAGKEELMKMRLPTRSDMICGYACLKG  92

351 NVSWRDRTRGSIFITELITCFQKYSCCCHLMEIFRKVQKSFEVPXAKAQM 400
    |.. |: .||| :|..|.  .| ..| |: ::: ||.  :. . : |.
 93 NAAMRNTKRGSWYIEALTQVFSERACDMHVADMLVKVNALIKEREGYAPG 142

401 PTIER........ATLTRDFYLFPGN*...  419
    ..:.|          .||..::|||||
143 TEFHRCKEMSEYCSTLCQQLYLFPGYPPT*  172
```

FIG.4

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGGCCACTTC  CAAGGATGCT  GGA                                                23
```

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CTGGAAGATG  GTGTCATAAA  GCAGC                                              25
```

( 2 ) INFORMATION FOR SEQ ID NO:3:

( i ) SEQUENCE CHARACTERISTICS:
        ( A ) LENGTH: 1414 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGGCAAAAAA  AAAAGGCGTA  AGAATTTTGA  AGCTATGTTC  AAAGGTATCC  TTCAGAGTGG     60
ATTGGATAAC  TTCGTGATAA  ACCACATGCT  AAAGAACAAC  GTGGCTGGAC  AAACATCTAT    120
CCAGACCCTA  GTACCTAATA  CGGATCAAAA  GTCGACCAGT  GTAAAAAAAG  ACAACCACAA    180
AAAAAAAACA  GTTAAGATGT  TGGAATACCT  GGGCAAAGAT  GTTCTTCATG  GTGTTTTTAA    240
TTATTTGGCA  AAACACGATG  TTCTGACATT  GAAGGAAGAG  GAAAAGAAAA  AATATTATGA    300
TGCCAAAATT  GAAGACAAGG  CCCTGATCTT  GGTAGACTCT  TTGCGAAAGA  ATCGCGTGGC    360
TCATCAAATG  TTTACCCAAA  CACTTCTCAA  TATGGACCAA  AAGATCACCA  GTGTAAAACC    420
TCTTCTGCAA  ATCGAGGCTG  GACCACCTGA  GTCAGCAGAA  TCTACAAATA  TACTCAAACT    480
TTGTCCTCGT  GAAGAATTCC  TGAGACTGTG  TAAAAAAAAT  CATGATGAGA  TCTATCCAAT    540
```

-continued

| | | | | | |
|---|---|---|---|---|---|
| AAAAAAGAGA | GAGGACCGCA | GACGCCTGGC | TCTCATCATA | TGCAATACAA | AGTTTGATCA | 600 |
| CCTGCCTGCA | AGGAATGGGG | CTCACTATGA | CATCGTGGGG | ATGAAAAGGC | TGCTTCAAGG | 660 |
| CCTGGGCTAC | ACTGTGGTTG | ACGAAAAGAA | TCTCACAGCC | AGGGATATGG | AGTCAGTGCT | 720 |
| GAGGGCATTT | GCTGCCAGAC | CAGAGCACAA | GTCCTCTGAC | AGCACGTTCT | TGGTACTCAT | 780 |
| GTCTCATGGC | ATCCTAGAGG | GAATCTGCGG | AACTGCGCAT | AAAAGAAAA | AACCGGATGT | 840 |
| GCTGCTTTAT | GACACCATCT | TCCAGATATT | CAACAACCGC | AACTGCCTCA | GTCTAAAGGA | 900 |
| CAAACCCAAG | GTCATCATTG | TCCAGGCCTG | CAGAGGTGAA | AAACATGGGG | AACTCTGGGT | 960 |
| CAGAGACTCT | CCAGCATCCT | TGGCAGTCAT | CTCTTCACAG | TCATCTGAGA | ACCTGGAGGC | 1020 |
| AGATTCTGTT | TGCAAGATCC | ACGAGGAGAA | GGACTTCATT | GCTTTCTGTT | CTTCAACACC | 1080 |
| ACATAACGTG | TCCTGGAGAG | ACCGCACAAG | GGGCTCCATC | TTCATTACGG | AACTCATCAC | 1140 |
| ATGCTTCCAG | AAATATTCTT | GCTGCTGCCA | CCTAATGGAA | ATATTTCGGA | AGGTACAGAA | 1200 |
| ATCATTTGAA | GTTCCACAGG | CTAAAGCCCA | GATGCCCACC | ATAGAACGAG | CAACCTTGAC | 1260 |
| AAGAGATTTC | TACCTCTTTC | CTGGCAATTG | AAAATGAAAC | CACAGGCAGC | CCAGCCCTCC | 1320 |
| TCTGTCAACA | TCAAAGAGCA | CATTTACCAG | TATAGCTTGC | ATAGTCAATA | TTTGGTATTT | 1380 |
| CAATAAAAGT | AAAGACTGTA | AAAAAAAAAA | AAAA | | | 1414 |

( 2 ) INFORMATION FOR SEQ ID NO:4:

( i ) SEQUENCE CHARACTERISTICS:
( A ) LENGTH: 418 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

```
Met Phe Lys Gly Ile Leu Gln Ser Gly Leu Asp Asn Phe Val Ile Asn
 1               5                  10                  15

His Met Leu Lys Asn Asn Val Ala Gly Gln Thr Ser Ile Gln Thr Leu
            20                  25                  30

Val Pro Asn Thr Asp Gln Lys Ser Thr Ser Val Lys Lys Asp Asn His
        35                  40                  45

Lys Lys Lys Thr Val Lys Met Leu Glu Tyr Leu Gly Lys Asp Val Leu
    50                  55                  60

His Gly Val Phe Asn Tyr Leu Ala Lys His Asp Val Leu Thr Leu Lys
65                  70                  75                  80

Glu Glu Glu Lys Lys Tyr Tyr Asp Ala Lys Ile Glu Asp Lys Ala
                85                  90                  95

Leu Ile Leu Val Asp Ser Leu Arg Lys Asn Arg Val Ala His Gln Met
            100                 105                 110

Phe Thr Gln Thr Leu Leu Asn Met Asp Gln Lys Ile Thr Ser Val Lys
        115                 120                 125

Pro Leu Leu Gln Ile Glu Ala Gly Pro Pro Glu Ser Ala Glu Ser Thr
    130                 135                 140

Asn Ile Leu Lys Leu Cys Pro Arg Glu Glu Phe Leu Arg Leu Cys Lys
145                 150                 155                 160

Lys Asn His Asp Glu Ile Tyr Pro Ile Lys Lys Arg Glu Asp Arg Arg
                165                 170                 175

Arg Leu Ala Leu Ile Ile Cys Asn Thr Lys Phe Asp His Leu Pro Ala
            180                 185                 190

Arg Asn Gly Ala His Tyr Asp Ile Val Gly Met Lys Arg Leu Leu Gln
```

|   |   |   | 195 |   |   |   | 200 |   |   |   | 205 |   |   |   |
|---|---|---|---|---|---|---|---|---|---|---|---|---|---|---|
| Gly | Leu | Gly | Tyr | Thr | Val | Val | Asp | Glu | Lys | Asn | Leu | Thr | Ala | Arg | Asp |
|   | 210 |   |   |   |   | 215 |   |   |   |   | 220 |   |   |   |
| Met | Glu | Ser | Val | Leu | Arg | Ala | Phe | Ala | Ala | Arg | Pro | Glu | His | Lys | Ser |
| 225 |   |   |   |   | 230 |   |   |   |   | 235 |   |   |   |   | 240 |
| Ser | Asp | Ser | Thr | Phe | Leu | Val | Leu | Met | Ser | His | Gly | Ile | Leu | Glu | Gly |
|   |   |   |   | 245 |   |   |   |   | 250 |   |   |   |   | 255 |   |
| Ile | Cys | Gly | Thr | Ala | His | Lys | Lys | Lys | Lys | Pro | Asp | Val | Leu | Leu | Tyr |
|   |   |   | 260 |   |   |   |   | 265 |   |   |   |   | 270 |   |   |
| Asp | Thr | Ile | Phe | Gln | Ile | Phe | Asn | Asn | Arg | Asn | Cys | Leu | Ser | Leu | Lys |
|   |   | 275 |   |   |   |   | 280 |   |   |   |   | 285 |   |   |   |
| Asp | Lys | Pro | Lys | Val | Ile | Ile | Val | Gln | Ala | Cys | Arg | Gly | Glu | Lys | His |
|   | 290 |   |   |   |   | 295 |   |   |   |   | 300 |   |   |   |   |
| Gly | Glu | Leu | Trp | Val | Arg | Asp | Ser | Pro | Ala | Ser | Leu | Ala | Val | Ile | Ser |
| 305 |   |   |   |   | 310 |   |   |   |   | 315 |   |   |   |   | 320 |
| Ser | Gln | Ser | Ser | Glu | Asn | Leu | Glu | Ala | Asp | Ser | Val | Cys | Lys | Ile | His |
|   |   |   |   | 325 |   |   |   |   | 330 |   |   |   |   | 335 |   |
| Glu | Glu | Lys | Asp | Phe | Ile | Ala | Phe | Cys | Ser | Ser | Thr | Pro | His | Asn | Val |
|   |   |   | 340 |   |   |   |   | 345 |   |   |   |   | 350 |   |   |
| Ser | Trp | Arg | Asp | Arg | Thr | Arg | Gly | Ser | Ile | Phe | Ile | Thr | Glu | Leu | Ile |
|   |   | 355 |   |   |   |   | 360 |   |   |   |   | 365 |   |   |   |
| Thr | Cys | Phe | Gln | Lys | Tyr | Ser | Cys | Cys | Cys | His | Leu | Met | Glu | Ile | Phe |
|   | 370 |   |   |   |   | 375 |   |   |   |   | 380 |   |   |   |   |
| Arg | Lys | Val | Gln | Lys | Ser | Phe | Glu | Val | Pro | Xaa | Ala | Lys | Ala | Gln | Met |
| 385 |   |   |   |   | 390 |   |   |   |   | 395 |   |   |   |   | 400 |
| Pro | Thr | Ile | Glu | Arg | Ala | Thr | Leu | Thr | Arg | Asp | Phe | Tyr | Leu | Phe | Pro |
|   |   |   |   | 405 |   |   |   |   | 410 |   |   |   |   | 415 |   |
| Gly | Asn |   |   |   |   |   |   |   |   |   |   |   |   |   |   |

DNA ENCODING PRECURSOR OF INTERLEUKIN-1 BETA CONVERTING ENZYME - RELATED CYSTEINE PROTEINASE III (ICE REL-III)

BACKGROUND OF THE INVENTION

Interleukin-1β (IL-1β) is a major mediator of chronic and acute intimation. Along with IL-1β, human monocytes produce two additional members of the IL-1 gene family; interleukin-1α (IL-1α) and IL-1 receptor antagonist (IL-RA). All three proteins bind to the membrane-anchored forms of the type 1 and type 2 IL-1 receptors (IL1R) on target cells. IL-1α and IL-1β elicit virtually identical biological responses whereas IL-1RA blocks these effects. Both IL-1α and IL1β are synthesized as 31 kDa primary translation products which lack functional hydrophobic signal sequences. The 31 kDa form of IL-1α is fully active without further processing but does not appear to be actively released from cells. IL-1β, the predominant form of IL-1 released by activated monocytes, is synthesized as an inactive 31 kDa precursor (pIL-1β) that is processed to its mature 17.5 kDa form (mIL-1β) by interleukin-1β converting enzyme (ICE), a novel cysteine proteinase. ICE generates fully active mIL-1β by cleaving pIL-1β between $Asp_{116}$ and $Ala_{117}$, a unique site for prohormone processing. The sequence around this cleavage site, -Tyr-Val-His-Asp-Ala-, is evolutionarily conserved in all known pIL-1β polypeptides.

Active human ICE as shown by conventional HPLC and affinity purification techniques is a heterodimer consisting of a 1:1 stoichiometric complex of 19,866 Da (p20) and 10,244 Da (p10) subunits. Cloned cDNAs have revealed that ICE is constituitively expressed as a 45 kDa proenzyme (p45) composed of a 14 kDa prodomain, followed by p20 which contains the active site $Cys_{285}$, a 19 residue connecting peptide that is not present in the mature enzyme, and p10, a required component of the active enzyme. The mature subunits are flanked by Asp-X sequences. Mutational analysis of these sites and expression in heterologous systems indicates that the generation of active enzyme is autocatalytic. Murine and rat ICE have also been cloned and show a high degree of sequence similarity including these structural motifs.

Recently, a family of ICE-like genes has begun to emerge, including the nematode cell death abnormal gene (CED-3) of *Caenorhabiditis elegans, Caenorhabiditis briggsae* and *Caenorhabiditis vulgaris*, and the murine neuronal precursor cell embroyonic developmentally downregulated (NEDD-2) gene. The predicted polypeptide sequences of these genes exhibit 29% and 27% sequence identity with human ICE, respectively. The sequence identity of CED-3 with ICE is higher in the regions corresponding to the p20 and p10 subunits of mature human ICE. All known sequences for ICE and for CED-3 contain the pentapeptide sequence -Gln-Ala-Cys-Arg-Gly-surrounding the catalytic cysteine of ICE or its equivalent in CED-3.

Both CED-3 and murine ICE, when expressed by transfection in fibroblast cell lines or by microinjection into neuronal cells, cause programmed cell death (apoptosis) to occur. The pro-apoptotic effects of CED-3 or ICE can be prevented by co-transfection with either bcl-2, a mammalian proto-oncogene which appears to function as a cell death suppressor gene, or with the cytokine response modifier A (crmA) gene product, a serpin-like inhibitor of ICE.

SUMMARY OF THE INVENTION

A novel human thiol proteinase termed $ICE_{rel}$-III (interleukin-1β convening enzyme—related cysteine proteinase III) has been isolated and purified. A DNA molecule encoding the full length precursor form of the $ICE_{rel}$-III protein has been isolated, purified and the nucleotide sequence determined. The $ICE_{rel}$-III encoding DNA has been cloned for expression in recombinant hosts. The DNA clones produce recombinant full-length $ICE_{rel}$-III and the individual subunits of the mature form of the enzyme. Recombinant $ICE_{rel}$-III is useful for identifying modulators of $ICE_{rel}$-III activity and hence modifiers of pathological conditions related to the pro-inflammatory or pro-apoptotic effects of $ICE_{rel}$-III. $ICE_{rel}$-III antisense molecules are useful for therapeutically reducing or eliminating the pro-inflammatory or pro-apoptotic effects of $ICE_{rel}$-III, whereas gene transplantation or gene therapy with $ICE_{rel}$-III is useful for enhancing the pro-inflammatory or pro-apoptotic effects of $ICE_{rel}$-III. These therapies are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease and Alzheimer's disease.

BRIEF DESCRIPTION OF THE DRAWINGS

FIG. 1. Nucleotide sequence of human $ICE_{rel}$-III (cDNA clone T17.1.1), its complementary nucleotide sequence, and deduced amino acid sequence.

FIG. 2. Alignment of the human $ICE_{rel}$-III amino acid sequence with the amino acid sequence of human ICE. Identical amino acids are indicated by a vertical line between the aligned sequences, whereas highly conservative amino acid differences are indicated by a double dot and conservative amino acid differences are indicated by a single dot between the aligned sequences.

FIG. 3. Alignment of the human $ICE_{rel}$-III amino acid sequence with the amino acid sequence of *Caenorhabiditis elegans* CED-3. Identical amino acids are indicated by a vertical line between the aligned sequences, whereas highly conservative amino acid differences are indicated by a double dot and conservative amino acid differences are indicated by a single dot between the aligned sequences.

FIG. 4. Alignment of the human $ICE_{rel}$-III amino acid sequence with the amino acid sequence of murine NEDD-2. Identical amino acids are indicated by a vertical line between the aligned sequences, whereas highly conservative amino acid differences are indicated by a double dot and conservative amino acid differences are indicated by a single dot between the aligned sequences.

DETAILED DESCRIPTION OF THE INVENTION

A complementary DNA (cDNA) which encodes the full length form of $ICE_{rel}$-III is identified, sequenced and isolated. The cDNA is cloned into expression vectors for expression in a recombinant host. The cDNA is useful to produce recombinant full length $ICE_{rel}$-III. The cDNA and the recombinant $ICE_{rel}$-III protein derived therefrom are useful in the production of antibodies, diagnostic kits, laboratory reagents and assays. The cDNA and the recombinant $ICE_{rel}$-III protein may be used to identify compounds that affect $ICE_{rel}$-III function, inflammation and cell apoptosis. $ICE_{rel}$-III antisense oligonucleotides or antisense mimetics may be clinically useful for reducing the expression of ICE$_{rel}$-III protein and thereby reducing the pro-inflammatory or pro-apoptotic effects of ICE$_{rel}$-III. Similarly, the ICE$_{rel}$-III coding sequence can be used for gene therapy to introduce ICE$_{rel}$-III into target cells thereby enhancing the pro-inflammatory or pro-apoptotic effects of ICE$_{rel}$-III.

A variety of cells and cell lines may be suitable for use to isolate ICE$_{rel}$-III cDNA. Selection of suitable cells may be done by screening for ICE$_{rel}$-III activity in cell extracts or conditioned medium using conventional techniques. Cells which possess ICE$_{rel}$-III activity in this assay may be suitable for the isolation of ICE$_{rel}$-III cDNA.

A variety of procedures may be used to molecularly clone ICE$_{rel}$-III cDNA. These methods include, but are not limited to, direct functional expression of the ICE$_{rel}$-III gene following the construction of an ICE$_{rel}$-III-containing cDNA library in an appropriate expression vector system. Another method is to screen an ICE$_{rel}$-III-containing cDNA library constructed in a bacteriophage or plasmid shuttle vector with a labelled oligonucleotide probe designed from the amino acid sequence of ICE$_{rel}$-III.

A variety of libraries constructed from cells may be useful for isolating ICE$_{rel}$-III-encoding DNA. Suitable libraries may be prepared from cells or cell lines which have ICE$_{rel}$-III activity.

Preparation of cDNA libraries can be performed by standard techniques. Such cDNA library construction techniques as well as other standard molecular biology techniques can be found, for example, in Maniatis, T., Fritsch, E. F., Sambrook, J., Molecular Cloning: A Laboratory Manual (Cold Spring Harbor Laboratory, Cold Spring Harbor, N.Y., 1982) or in Ausubel, F. M., Brent, R., Kingston, R. E., Moore, D. D., Seidman, J. G., Smith, J. A., Struhl, K., Current Protocols in Molecular Biology (John Wiley & Sons, New York, N.Y., 1989).

DNA encoding ICE$_{rel}$-III may also be isolated from a suitable genomic DNA library. Construction of genomic DNA libraries can be performed by standard techniques known, such as those described in Maniatis, T. et al., (supra) and Ausubel et al., (supra).

The cloned ICE$_{rel}$-III cDNA may be recombinantly expressed by molecular cloning into an expression vector containing a suitable promoter and other appropriate transcription regulatory elements, and transferred into prokaryotic or eukaryotic host cells to produce recombinant ICE$_{rel}$-III.

Expression vectors are defined herein as DNA sequences that are required for the transcription of cloned copies of genes and the translation of their mRNAs in an appropriate host. Such vectors can be used to express eukaryotic genes in a variety of hosts such as bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant ICE$_{rel}$-III in mammalian cells. Commercially-available mammalian expression vectors which may be suitable for recombinant ICE$_{rel}$-III expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

DNA encoding ICE$_{rel}$-III may also be cloned into an expression vector for expression in a recombinant host cell. Recombinant host cells may be prokaryotic or eukaryotic, including but not limited to bacteria, yeast, mammalian cells and insect cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techinques including but not limited to transformation, transfection, infection, protoplast fusion, and electroporation. The expression vector-containing cells are clonally propagated and individually analyzed to determine whether they produce ICE$_{rel}$-III protein. Identification of ICE$_{rel}$-III expressing host cell clones may be done by several means, including but not limited to immunological reactivity with anti-ICE$_{rel}$-III antibodies, and the presence of host cell-associated ICE$_{rel}$-III activity.

Expression of ICE$_{rel}$-III cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the ICE$_{rel}$-III cDNA sequence(s) that yields optimal levels of enzymatic activity and/or ICE$_{rel}$-III protein, modifed ICE$_{rel}$-III cDNA molecules are constructed. Host cells are transformed with the cDNA molecules and the levels of ICE$_{rel}$-III RNA and protein are measured.

Levels of ICE$_{rel}$-III protein in host cells are quantitated by a variety of methods such as immunoaffinity and/or ligand affinity techniques. ICE$_{rel}$-III-specific affinity beads or ICE$_{rel}$-III-specific antibodies are used to isolate $^{35}$S-methionine labelled or unlabelled ICE$_{rel}$-III protein. Labelled ICE$_{rel}$-III protein is analyzed by SDS-PAGE. Unlabelled ICE$_{rel}$-III protein is detected by Western blotting, ELISA or RIA assays employing ICE$_{rel}$-III specific antibodies.

Following expression of ICE$_{rel}$-III in a recombinant host cell, ICE$_{rel}$-III protein may be recovered to provide ICE$_{rel}$-III in active form. Several ICE$_{rel}$-III purification procedures are available and suitable for use. Recombinant ICE$_{rel}$-III may be purified from cell lysates or from conditioned culture media, by various combinations of, or individual application of fractionation, or chromatography steps that are known in the art.

In addition, recombinant ICE$_{rel}$-III can be separated from other cellular proteins by use of an immuno-affinity column made with monoclonal or polyclonal antibodies specific for full length nascent ICE$_{rel}$-III or polypeptide fragments of ICE$_{rel}$-III.

The recombinant protein may be used to generate antibodies. The term "antibody" as used herein includes both polyclonal and monoclonal antibodies, as well as fragments thereof, such as, Fv, Fab and F(ab)2 fragments that are capable of binding antigen or hapten.

Monospecific antibodies to $ICE_{rel}$-III are purified from mammalian antisera containing antibodies reactive against $ICE_{rel}$-III or are prepared as monoclonal antibodies reactive with $ICE_{rel}$-III using standard techniques. Monospecific antibody as used herein is defined as a single antibody species or multiple antibody species with homogenous binding characteristics for $ICE_{rel}$-III. Homogenous binding as used herein refers to the ability of the antibody species to bind to a specific antigen or epitope, such as those associated with the $ICE_{rel}$-III, as described above. Enzyme-specific antibodies are raised by immunizing animals such as mice, rats, guinea pigs, rabbits, goats, horses and the like, with rabbits being preferred, with an appropriate concentration of $ICE_{rel}$-III either with or without an immune adjuvant.

Monoclonal antibodies (mAb) reactive with $ICE_{rel}$-III may be prepared by conventional methods, such as by immunizing inbred mice with $ICE_{rel}$-III. The mice are immunized with about 0.1 mg to about 10 mg, preferably about 1 mg, of $ICE_{rel}$-III in about 0.5 ml buffer or saline incorporated in an equal volume of an acceptable adjuvant. Freund's complete adjuvant is preferred. The mice receive an initial immunization on day 0 and are rested for about 3 to about 30 weeks. Immunized mice are given one or more booster immunizations of about 0.1 to about 10 mg of $ICE_{rel}$-III in a buffer solution such as phosphate buffered saline (PBS) by the intravenous (IV) route. Lymphocytes from antibody-positive mice are obtained by removing spleens from immunized mice by standard procedures known in the art. Hybridoma cells are produced by mixing the splenic lymphocytes with an appropriate fusion partner under conditions which will allow the formation of stable hybridomas. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody produciton by an immunoassay such as solid phase immunoradioassay (SPIRA) using $ICE_{rel}$-III as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

In vitro production of anti-$ICE_{rel}$-III mAb is carded out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of $ICE_{rel}$-III in body fluids or tissue and cell extracts.

The above described methods for producing monospecific antibodies may be utilized to produce antibodies specific for $ICE_{rel}$-III polypeptide fragments or full-length nascent $ICE_{rel}$-III polypeptide.

$ICE_{rel}$-III antibody affinity columns are made by adding the antibodies to a gel support, such as Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing $ICE_{rel}$-III or $ICE_{rel}$-III fragments are slowly passed through the column. The column is then washed, and the protein is eluted. The purified $ICE_{rel}$-III protein is then dialyzed against phosphate buffered saline.

Kits containing $ICE_{rel}$-III cDNA, $ICE_{rel}$-III RNA, antibodies to $ICE_{rel}$-III or $ICE_{rel}$-III protein may be prepared. Such kits are used to detect DNA or RNA which hybridizes to $ICE_{rel}$-III DNA or to detect the presence of $ICE_{rel}$-III protein or peptide fragments in a sample. Such characterization is useful for a variety of purposes including but not limited to forensic analyses and epidemiological studies.

The DNA molecules, RNA molecules, recombinant proteins and antibodies of the present invention may be used to screen and measure levels of $ICE_{rel}$-III DNA, $ICE_{rel}$-III RNA or $ICE_{rel}$-III protein. The recombinant promins, DNA molecules, RNA molecules and antibodies lend themselves to the formulation of kits suitable for the detection and typing of $ICE_{rel}$-III. Such a kit would comprise a compartmentalized carrier suitable to hold in close confinement at least one container. The carder would further comprise reagents such as recombinant $ICE_{rel}$-III protein or anti-$ICE_{rel}$-III antibodies suitable for detecting $ICE_{rel}$-III. The carder may also contain means for detection such as labeled antigen or enzyme substrates or the like.

Nucleotide sequences that are complementary to the $ICE_{rel}$-III encoding cDNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other $ICE_{rel}$-III antisense oligonucleotide mimetics. $ICE_{rel}$-III antisense molecules may be introduced into cells by microinjection, liposome encapsulation or by expression from vectors harbouring the antisense sequence. $ICE_{rel}$-III antisense therapy may be particularly useful for the treatment of diseases where it is beneficial to reduce $ICE_{rel}$-III acitivy.

$ICE_{rel}$-III gene therapy may be used to introduce $ICE_{rel}$-III into the cells of target organs. The $ICE_{rel}$-III gene can be ligated into viral vectors which mediate transfer of the $ICE_{rel}$-III DNA by infection of recipient host cells. Suitable viral vectors include retrovirus, adenovirus, adeno-associated virus, herpes virus, vaccinia virus, polio virus and the like. Alternatively, $ICE_{rel}$-III DNA can be transferred into cells for gene therapy by non-viral techniques including receptor-mediated targetted DNA transfer using ligand-DNA conjugates or adenovirus-ligand-DNA conjugates, lipofection membrane fusion or direct microinjection. These procedures and variations of them are suitable for ex vivo as well as in vivo $ICE_{rel}$-III gene therapy. $ICE_{rel}$-III gene therapy may be particularly useful for the treatment of diseases where it is beneficial to elevate $ICE_{rel}$-III activity.

Pharmaceutically useful compositions comprising $ICE_{rel}$-III DNA or $ICE_{rel}$-III protein may be formulated according to known methods such as by the admixture of a pharmaceutically acceptable carrier. Examples of such carders and methods of formulation may be found in Remington's Pharmaceutical Sciences. To form a pharmaceutically acceptable composition suitable for effective administration, such compositions will contain an effective amount of the protein or DNA.

Therapeutic or diagnostic compositions of the invention are administered to an individual in amounts sufficient to treat or diagnose ICE$_{rel}$-III related disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

Because the genetic code is degenerate, more than one codon may be used to encode a particular amino acid, and therefore, the amino acid sequence can be encoded by any of a set of similar DNA oligonucleotides. Only one member of the set will be identical to the ICE$_{rel}$-III sequence but will be capable of hybridizing to ICE$_{rel}$-III DNA even in the presence of DNA oligonucleotides with mismatches. The mismatched DNA oligonucleotides may still hybridize to the ICE$_{rel}$IIIDNA to permit identification and isolation of ICE$_{rel}$-III encoding DNA.

DNA encoding ICE$_{rel}$-III from a particular organism may be used to isolate and purify homologues of ICE$_{rel}$-III from other organisms. To accomplish this, the first ICE$_{rel}$-III DNA may be mixed with a sample containing DNA encoding homologues of ICE$_{rel}$-III under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate.

As used herein, a "functional derivative" of ICE$_{rel}$-III is a compound that possesses a biological activity (either functional or structural) that is substantially similar to the biological activity of ICE$_{rel}$III. The term "functional derivatives" is intended to include the "fragments," "variants," "degenerate variants," "analogs" and "homologs" or to "chemical derivatives" of ICE$_{rel}$-III. The term "fragment" is meant to refer to any polypeptide subset of ICE$_{rel}$-III. The term "variant" is meant to refer to a molecule substantially similar in structure and function to either the entire ICE$_{rel}$-III molecule or to a fragment thereof. A molecule is "substantially similar" to ICE$_{rel}$-III if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire ICE$_{rel}$-III molecule or to a fragment thereof.

The term "chemical derivative" describes a molecule that contains additional chemical moieties which are not normally a part of the base molecule. Such moieties may improve the solublity, half-life, absorption, etc of the base molecule. Alternatively the moieties may attenuate undesirable side effects of the base molecule or decrease the toxicity of the base molecule. Examples of such moieties are described in a variety of texts, such as Remington's Pharmaceutical Sciences.

The present invention is also directed to methods for screening for compounds which modulate that expression of DNA or RNA encoding ICE$_{rel}$-III as well as the function of ICE$_{rel}$-III protein in vivo. Compounds which modulate these activities may be DNA, RNA, peptides, proteins, or non-proteinaceous organic molecules. Compounds may modulate by increasing or attenuating the expression of DNA or RNA encoding ICE$_{rel}$-III or the function of ICE$_{rel}$-III protein. Compounds that modulate the expression of DNA or RNA encoding ICE$_{rel}$-III or the function of ICE$_{rel}$-III protein may be detected by a variety of assays. The assay may be a simple "yes/no" assay to determine whether there is a change in expression or function. The assay may be made quantitative by comparing the expression or function of a test sample with the levels of expression or function in a standard sample.

The following examples illustrate the present invention without, however, limiting the same thereto.

EXAMPLE 1

MOLECULAR CLONING OF ICE$_{rel}$-III

A full-length cDNA clone for ICE$_{rel}$-III was identified by replica-filter screening of a THP1 cell (acute monocytic leukemia cell line; ATCC TIB 202) cDNA library in bacteriophage lgt10 using the [$^{32}$P]labelled synthetic oligonucleotide probes:

(5')AGG CCA CTT CCA AGG ATG CTG GA(3'); SEQ ID NO: 1 for one replica filter; and (5')CTG GAA GAT GGT GTC ATA AAG CAG C(3'); SEQ ID NO:2 for the other paired replica filter.

The largest clone identified, designated T17.1.1, was 1414 bp. The clone was retrieved from lgt10 following expansion of the 1 bacteriophage by culture on *Escherichia coli*-containing agarose plates, then purifying the 1 bacteriophage DNA by a combination of polyethylene glycol precipitation, macroporous silica-gel chromatography and alcohol precipitation. The T17.1.1 DNA fragment was excised by partial Eco RI restriction digestion (partial digestion was necessary owing to an internal Eco RI site in the T17.1.1 sequence) followed by agarose gel purification of the 1.4 Kb fragment then ligation of the purified fragment into the Eco RI site of the plasmid vector pBluescript II SK+ (Stratagene). Following transformation into competent *E. coli* cells, colony purification and propagation of the resulting transformed cells in liquid culture, the plasmid DNA was purified and the nucleotide sequence of the clone T17.1.1 insert was determined by dideoxy DNA sequencing.

The complete cDNA sequence of ICE$_{rel}$-III (clone T17.1.1) and corresponding amino acid sequence is shown in FIG. 1. The longest open reading frame of ICE$_{rel}$-III clone T17.1.1 (bases 35 to 1288) encodes a 47.7 kDa polypeptide which has 51% sequence identity (65% sequence similarity) with human interleukin-1β converting enzyme (FIG. 2), 24% sequence identity (49% sequence similarity) with the *Caenorhabiditis elegans* CED-3 polypeptide (FIG. 3) and 24% sequence identity (45% sequence similarity) with the murine NEDD-2 polypeptide (FIG. 4). The particularly high degree of sequence conservation surrounding the catalytic cysteine residue ($Cys_{299}$ of $ICE_{rel}$-III, $Cys_{285}$ of human interleukin-1β converting enzyme, $Cys_{358}$ of CED-3) as well as other structural motifs throughout the polypeptide is consistent with $ICE_{rel}$-III being a thiol proteinase.

EXAMPLE 2

SUB-CLONING OF THE $ICE_{rel}$-III cDNA INTO EXPRESSION VECTORS

The cDNA encoding $ICE_{rel}$-III was sub-cloned into several vectors for expression of the $ICE_{rel}$-III protein in transfected host cells and for in vitro transcription/translation. These vectors include pBluescript II SK+ (where expression is driven by T7 or T3 promoters) pcDNA I/Amp (where expression is driven by the cytomegalovirus (CMV) promoter), pSZ9016-1 (where expression is driven by the HIV long terminal repeat (LTR) promoter) and the baculovirus transfer vector pVL1393 (where expression is driven by the polyhedrin (PH) promoter) for producing recombinant baculovirus containing the $ICE_{rel}$-III encoding DNA sequence. The predicted/actual amino acid sequence of $ICE_{rel}$-III is shown in FIG. 1.

a) pBluescript II SK+:$ICE_{rel}$-III. The full length $ICE_{rel}$-III cDNA clone was retrieved from lambda bacteriophage by limited Eco RI digestion and ligated into Eco RI-cut, CIP-treated pBluescript II SK+. Separate subclones were recovered in which the sense orientation of $ICE_{rel}$-III followed either the T7 or T3 promoters.

b) pcDNA I/Amp:$ICE_{rel}$-III. To facilitate directional cloning, $ICE_{rel}$-III was excised from a purified plasmid preparation of pBluescript II SK+:$ICE_{rel}$-III in which the $ICE_{rel}$-III DNA sequence was downstream of the T7 promoter using Eco RV and Xba I. The resulting Eco RV, Xba I $ICE_{rel}$-III fragment was purified and ligated into Eco RV-cut, Xba I-cut, CIP-treated pcDNA I/Amp such that the $ICE_{rel}$-III encoding DNA was downstream of the CMV promoter.

c) pSZ9016-1 :$ICE_{rel}$-III. $ICE_{rel}$-III was excised from pBluescript II SK+:$ICE_{rel}$-III by limited Eco RI digestion and subsequent purification of the 1.3 Kb fragment from agarose gels. The resulting Eco RI $ICE_{rel}$-III fragment was ligated into Eco RI-cut, CIP-treated pSZ9016-1. Subclones were selected in which the sense orientation of $ICE_{rel}$-III was downstream of the HIV LTR promoter.

d) pVL1393:$ICE_{rel}$-III and pVL1393:T7 $ICE_{rel}$-III HA Directional cloning of the $ICE_{rel}$-III encoding DNA into the baculovirus transfer vector pVL1393 was mediated by excising $ICE_{rel}$-III from pcDNA I/Amp:$ICE_{rel}$-III with Bam HI and Xba I then ligating the resulting 1.3 Kb fragment into Bam HI-cut, Xba I-cut, CIP-treated pVL1393 producing pVL1393:$ICE_{rel}$-III. Similarly, $ICE_{rel}$-III was epitope tagged by engineering a T7 tag at the 5' amino terminus of the $ICE_{rel}$-III open reading frame and a FluHA epitope at the 3' carboxy terminus. The $ICE_{rel}$-III DNA modified in this manner was ligated into the Bam HI/Xba I sites of pVL1393 to produce pVL1393:T7 $ICE_{rel}$-III HA.

EXAMPLE 3

EXPRESSION OF THE $ICE_{rel}$-III POLYPEPTIDE BY in vitro TRANSCRIPTION/TRANSLATION AND BY TRANSFECTION INTO HOST CELLS Vectors containing the $ICE_{rel}$-II encoding DNA sequence were used to drive the translation of the $ICE_{rel}$-III polypeptide in rabbit reticulocyte lysates, mammalian host cells, and in baculovirus infected insect cells. The experimental procedures were essentially those outlined in the manufacturers' instructions.

a) In vitro Transcription/Translation. pBluescript III SK+:$ICE_{rel}$-III plasmid DNA (with $ICE_{rel}$-III in the T7 orientation) was linearized by Bam HI digestion downstream of the $ICE_{rel}$-III insert. The linearized plasmid was purified and used as a template for run-off transcription using T7 RNA polymerase in the presence of m7G(5')ppp(5')G. The resulting capped $ICE_{rel}$-III transcripts were purified by LiCl precipitation and used to drive the translation of $ICE_{rel}$-III in nuclease-pretreated rabbit reticulocyte lysate in the presence of L-[$^{35}$S] methionine. The resulting translation mixtures contained radiolabelled $ICE_{rel}$-III protein which migrated on SDS/polyacrylamide gels with an apparent molecular mass of 45±2 kDa.

b) Expression in Mammalian Cells. The $ICE_{rel}$-III protein was expressed in mammalian host cells following transfection with either pcDNA I/Amp:$ICE_{rel}$-III (under control of the CMV promoter) or pSZ9016-1:$ICE_{rel}$-III (under control of the HIV LTR promoter). In the latter case (pSZ9016-1:$ICE_{rel}$-III), cells were co-transfected with the TAT expressing plasmid pSZ90161:TAT. For both $ICE_{rel}$-III expression plasmids, COS-7 cells were transfected using either DEAE-dextran or lipofection with Lipofectamine (BRL).

c) Expression in Insect Cells. The $ICE_{rel}$-III containing baculovirus transfer vector pVL1393:T7 $ICE_{rel}$-III HA was used to produce recombinant baculovirus (*Autographa californica*) by in vivo homologous recombination. Epitope tagged $ICE_{rel}$-III was then expressed in Sf9 (*Spodoptera frugiperda*) insect cells grown in suspension culture following infection with the $ICE_{rel}$-III-containing recombinant baculovirus.

EXAMPLE 4

CLONING OF OF $ICE_{rel}$-III FOR EXPRESSION OF THE $ICE_{rel}$-III POLYPEPTIDE IN OTHER HOST CELL SYSTEMS a) Cloning of $ICE_{rel}$-III cDNA into a bacterial expression vector.

Recombinant $ICE_{rel}$-III is produced in a bacterium such as *E. coli* following the insertion of the optimal $ICE_{rel}$-III cDNA sequence into expression vectors designed to direct the expression of heterologous proteins. These vectors may be constructed such that recombinant $ICE_{rel}$-III is synthesized alone or as a fusion protein for subsequent manipulation. Similarly, expression may be controlled such that recombinant $ICE_{rel}$-III is recovered as a soluble protein or within insoluble inclusion bodies. Vectors such as pBR322, pSKF, pUR, pATH, pGEX, pT7-5, pT7-6, pT7-7, pET, pIBI (IBI), pSP6/T7-19 (Gibco/BRL), pBluescript II (Stratagene), pTZ18R, pTZ19R (USB), pSE420 (Invitrogen) or the like are suitable for these purposes.

b) Cloning of ICE$_{rel}$-III cDNA into a yeast expression vector

Recombinant ICE$_{rel}$-III is produced in a yeast such as *Saccharomyces cerevisiae* following the insertion of the optimal ICE$_{rel}$-III cDNA cistron into expression vectors designed to direct the intracellular or extracellular expression of heterologous proteins. In the case of intracellular expression, vectors such as EmBLyex4 or the like are ligated to the ICE$_{rel}$-III cistron [Rinas, U. et al., Biotechnology 8:543–545 (1990); Horowitz B. et al., J. Biol. Chem. 265:4189–4192 (1989)]. For extracellular expression, the ICE$_{rel}$-III cistron is ligated into yeast expression vectors which fuse a secretion signal (a yeast or mammalian peptide) to the amino terminus of the ICE$_{rel}$-III protein [Jacobson, M. A., Gene 85:511–516 (1989); Riett L. and Bellon N. Biochem. 28: 2941–2949 (1989)].

c) Cloning of ICE$_{rel}$-III cDNA into a viral expression vector

Recombinant ICE$_{rel}$-III is produced in mammalian host cells, such as HeLa S3 cells, after infection with vaccinia virus containing the ICE$_{rel}$III cDNA sequence. To produce ICE$_{rel}$-III:vaccinia virus, the ICE$_{rel}$-III cDNA is first ligated into a transfer vector, such as pSC11, pTKgptF1s, pMJ601 or other suitable vector, then transferred to vaccinia virus by homologous recombination. After plaque purification and virus amplification, ICE$_{rel}$-III:vaccinia virus is used to infect mammalian host cells and produce recombinant ICE$_{rel}$-III protein.

EXAMPLE 5

Process for the Production of a Interleukin-1β Convening Enzyme—Related Cysteine Proteinase III Polypeptide:

Recombinant ICE$_{rel}$-III is produced by a) transforming a host cell with the DNA encoding ICE$_{rel}$-III protein to produce a recombinant host cell;

b) culturing the recombinant host cell under conditions which allow the production of interleukin-1β converting enzyme—related cysteine proteinase III; and c) recovering the interleukin-1β converting enzyme—related cysteine proteinase III.

The recombinant interleukin-1β converting enzyme—related cysteine proteinase III is purified and characterized by standard methods.

EXAMPLE 6

Compounds that affect interleukin-1β converting enzyme—related cysteine proteinase III activity may be detected by a variety of methods. A method of identifying compounds that affect interleukin-1β converting enzyme—related cysteine proteinase III comprises:

(a) mixing a test compound with a solution containing interleukin-1β converting enzyme—related cysteine proteinase III to form a mixture;

(b) measuring interleukin-1β converting enzyme—related cysteine proteinase III activity in the mixture; and (c) comparing the interleukin-1β converting enzyme—related cysteine proteinase III activity in the mixture to a standard.

Compounds that affect interleukin-1β converting enzyme—related cysteine proteinase III activity may be formulated into pharmaceutical compositions. Such pharmaceutical compositions may be useful for treating diseases or conditions that are characterized by altered interleukin-1β converting enzyme—related cysteine proteinase III activity. Examples of diseases wherein the interleukin-1β converting enzyme—related cysteine proteinase III activity is increased include immune deficiency syndromes, pathogenic infections, cardiovascular and neurological injury, alopecia, aging, Parkinson's disease and Alzheimers disease. Treatment of such diseases comprises treatment with compounds that decrease the activity of interleukin-1β converting enzyme—related cysteine proteinase III. Examples of diseases wherein the interleukin-1β converting enzyme—related cysteine proteinase III activity is decreased include autoimmune diseases, leukemias, lymphomas and other cancers wherein the interleukin-1β converting enzyme—related cysteine proteinase III activity is decreased. Treatment of such diseases comprises treatment with compounds that increase the activity of interleukin-1β converting enzyme—related cysteine proteinase III activity.

EXAMPLE 7

DNA which is structurally related to DNA encoding interleukin-1β converting enzyme—related cysteine proteinase III is detected with a probe. A suitable probe may be derived from DNA having all or a portion of the nucleotide sequence of FIG. 1, RNA encoded by DNA having all or a portion of the nucleotide sequence of FIG. 1, degenerate oligonucleotides derived from a portion of the amino acid sequence of FIG. 1 or an antibody directed against interleukin-1β converting enzyme—related cysteine proteinase III.

EXAMPLE 8

A kit useful for the detection and characterization of DNA or RNA encoding interleukin-1β converting enzyme—related cysteine proteinase III or interleukin-1β converting enzyme—related cysteine proteinase III is prepared by conventional methods. The kit may contain DNA encoding interleukin-1β converting enzyme—related cysteine proteinase III, recombinant interleukin-1β converting enzyme—related cysteine proteinase III, RNA corresponding to the DNA encoding interleukin-1β converting enzyme—related cysteine proteinase III or antibodies to interleukin-1β converting enzyme—related cysteine proteinase III. The kit may be used to characterized test samples, such as forensic samples or epidemiological samples.

EXAMPLE 9

Cloning of other ICE$_{rel}$-III genes using human ICE$_{rel}$-III gene

The cross hybridization of the DNA representing portions of the ICE$_{rel}$-III gene to genomic DNA isolated from other organisms makes it possible to clone the homologous genes from the parent organisms. To do this, a genomic library from another primate such as a monkey is constructed from genomic DNA according to conventional methods. Using, for example, an EMBL vector, an EMBL genomic library is prepared, plated and screened by hybridization with a $^{32}$P-labeled DNA probe. Positive plaques are selected and subjected to additional screening until a purified cross-reacting plaque is selected. The DNA contained in the positive clone is further characterized by physical methods such as restriction mapping, Southern hybridization and DNA sequencing.

For example, purified nucleic acid encoding a functional interleukin-1β converting enzyme—related cysteine proteinase III from such an animal may be isolated by hybridizing an appropriate sample with nucleic acid encoding interleukin-1β converting enzyme—related cysteine proteinase III under low stringency conditions.

EXAMPLE 10

Use of mutagenized ICE$_{rel}$-III

DNA encoding ICE$_{rel}$-III is mutagenized using standard methods to produce an altered ICE$_{rel}$-III gene. Host cells are transformed with the altered ICE$_{rel}$-III to produce altered ICE$_{rel}$-III protein. The altered ICE$_{rel}$-III protein may be isolated, purified and used to characterize the function of ICE$_{rel}$-III protein.

What is claimed is:

1. An isolated DNA molecule which consists of SEQ ID NO:3.

2. An expression vector containing the DNA molecule of claim 1.

3. A host cell containing the expression vector of claim 2.

4. A pharmaceutical composition comprising the DNA molecule of claim 3.

* * * * *